United States Patent
Wong et al.

(10) Patent No.: US 10,076,442 B2
(45) Date of Patent: Sep. 18, 2018

(54) SYSTEMS AND METHODS FOR CONTROLLING VACUUM WITHIN PHACOEMULSIFICATION SYSTEMS

(71) Applicant: ABBOTT MEDICAL OPTICS INC., Santa Ana, CA (US)

(72) Inventors: Wayne S. Wong, Irvine, CA (US); Jon D. Jacobson, Irvine, CA (US); Tapan Patel, Chino Hills, CA (US); James W. Staggs, Laguna Niguel, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 127 days.

(21) Appl. No.: 15/184,627

(22) Filed: Jun. 16, 2016

(65) Prior Publication Data

US 2016/0367400 A1    Dec. 22, 2016

Related U.S. Application Data

(62) Division of application No. 13/236,386, filed on Sep. 19, 2011, now Pat. No. 9,393,152.

(51) Int. Cl.
  *A61F 9/007* (2006.01)
  *A61M 1/00* (2006.01)
  *A61B 17/00* (2006.01)

(52) U.S. Cl.
  CPC ........ *A61F 9/00745* (2013.01); *A61M 1/0031* (2013.01); *A61M 1/0058* (2013.01);
  (Continued)

(58) Field of Classification Search
  CPC ............ A61F 9/00745; A61M 1/0031; A61M 1/0058; A61M 2210/0612; A61B 2017/00977
  See application file for complete search history.

(56) References Cited

U.S. PATENT DOCUMENTS

| 5,700,240 A  | 12/1997 | Barwick, Jr. et al. |
| 7,670,330 B2 | 3/2010  | Claus et al. |

(Continued)

FOREIGN PATENT DOCUMENTS

| WO | 06101908 A2   | 9/2006 |
| WO | 2008060995 A1 | 5/2008 |

OTHER PUBLICATIONS

International Search Report and Written Opinion for Application No. PCT/US2012/052997, dated Oct. 29, 2012, 12 pages.

*Primary Examiner* — Imani Hayman
(74) *Attorney, Agent, or Firm* — Johnson & Johnson Surgical Vision, Inc.

(57) ABSTRACT

The invention relates to systems and methods for controlling vacuum within phacoemulsification systems. The phacoemulsification system may include a handpiece having a needle coupled to a power Source configured to cause the needle to be ultrasonically vibrated during operation, and an aspiration Source. The system includes a footpedal that defines a first position and a second position, and also includes a computer program product operatively coupled to the handpiece and the foot pedal, having a computer usable medium with a sequence of instructions which causes the processor to control power from the power source and vacuum from the aspiration source applied to the handpiece. The process provides a vacuum at a first level to the handpiece when the footpedal is at the first position; provides power to the handpiece when the footpedal is at the second position; and reduces the vacuum to a second level when the footpedal position transitions.

9 Claims, 12 Drawing Sheets

(52) U.S. Cl.
  CPC .............. *A61B 2017/00977* (2013.01); *A61M 2210/0612* (2013.01)

(56) References Cited

U.S. PATENT DOCUMENTS

| | | |
|---|---|---|
| 7,785,336 B2 | 8/2010 | Staggs |
| 2007/0073309 A1 | 3/2007 | Kadziauskas et al. |
| 2008/0114290 A1* | 5/2008 | King ................... A61F 9/00745 604/30 |
| 2009/0005712 A1 | 1/2009 | Raney |
| 2010/0280435 A1 | 11/2010 | Raney et al. |
| 2011/0098721 A1 | 4/2011 | Tran et al. |

\* cited by examiner

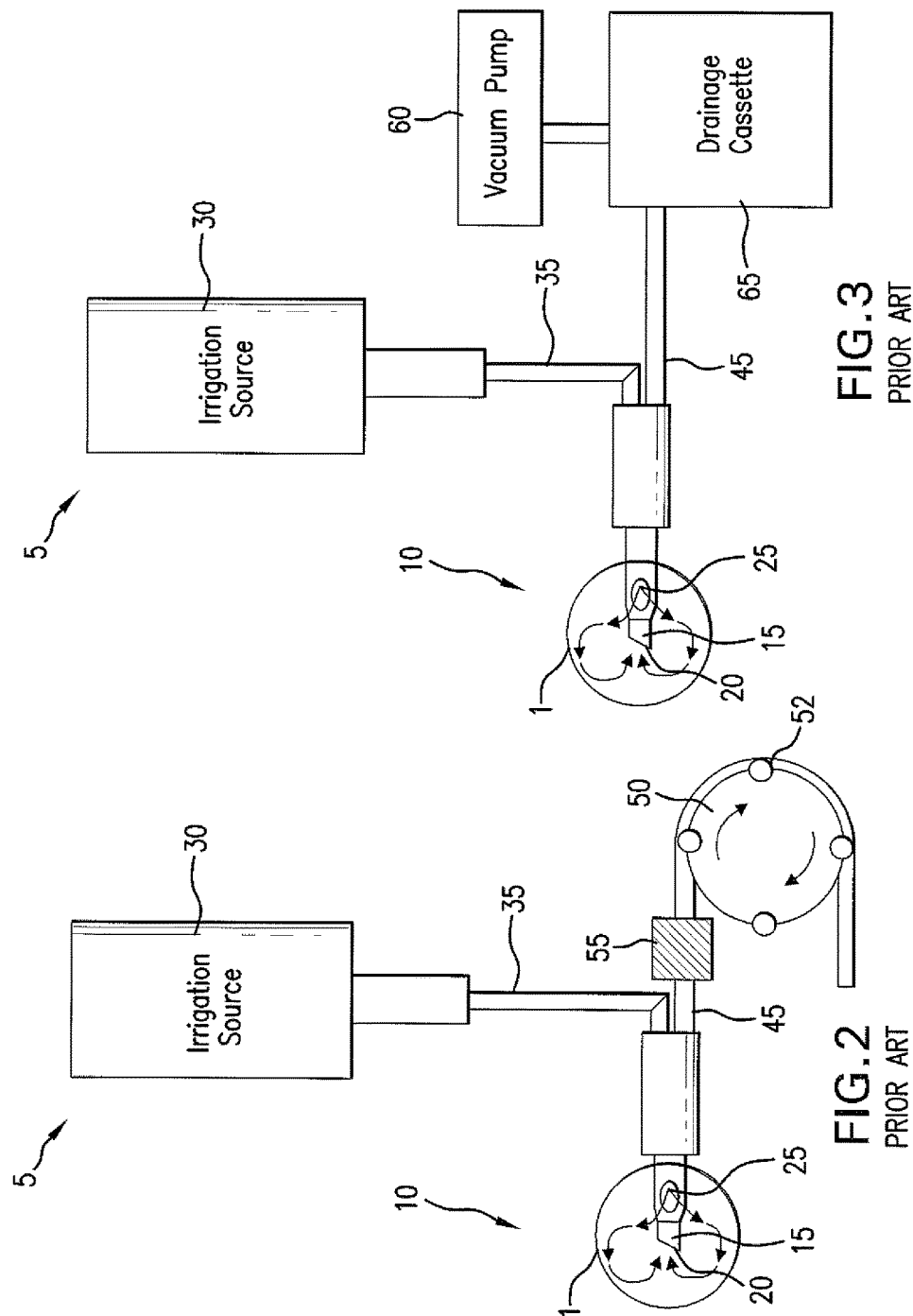

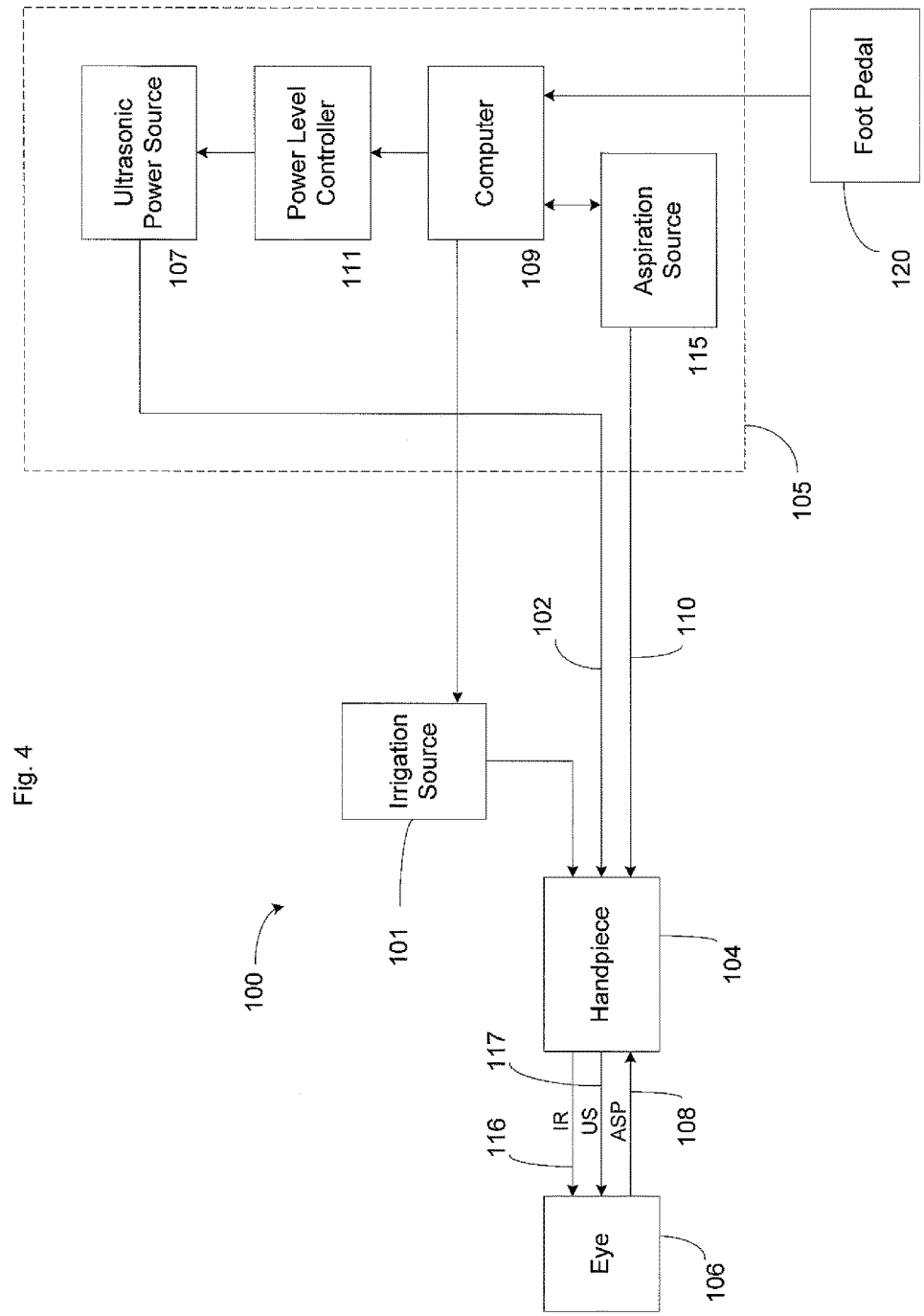

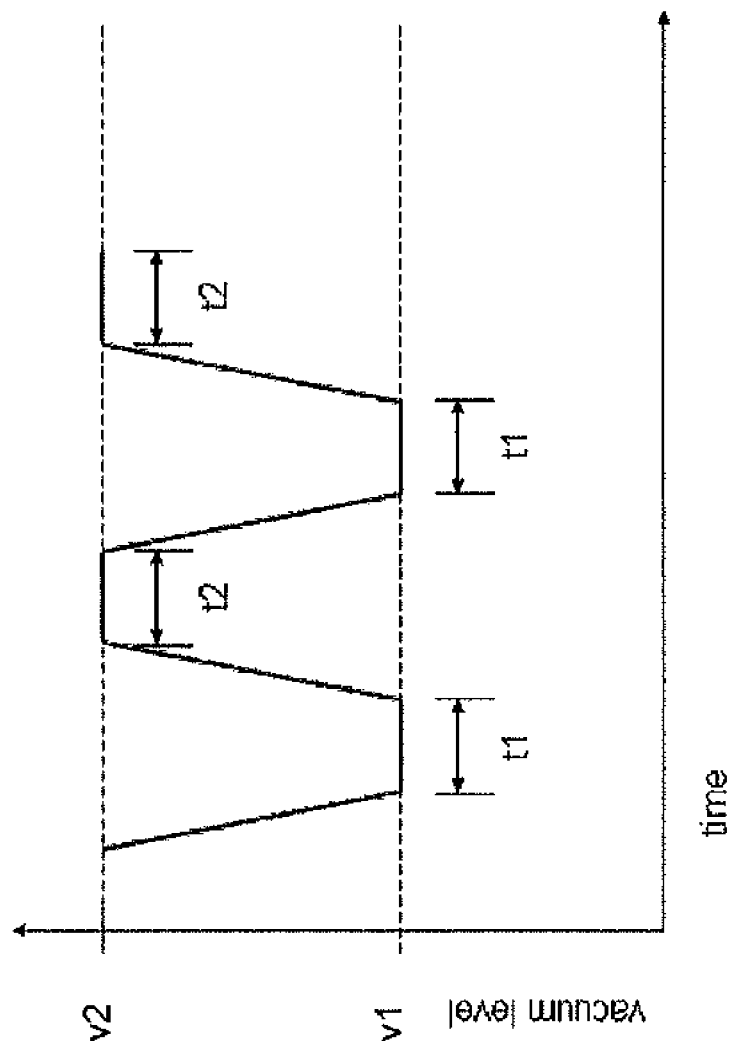

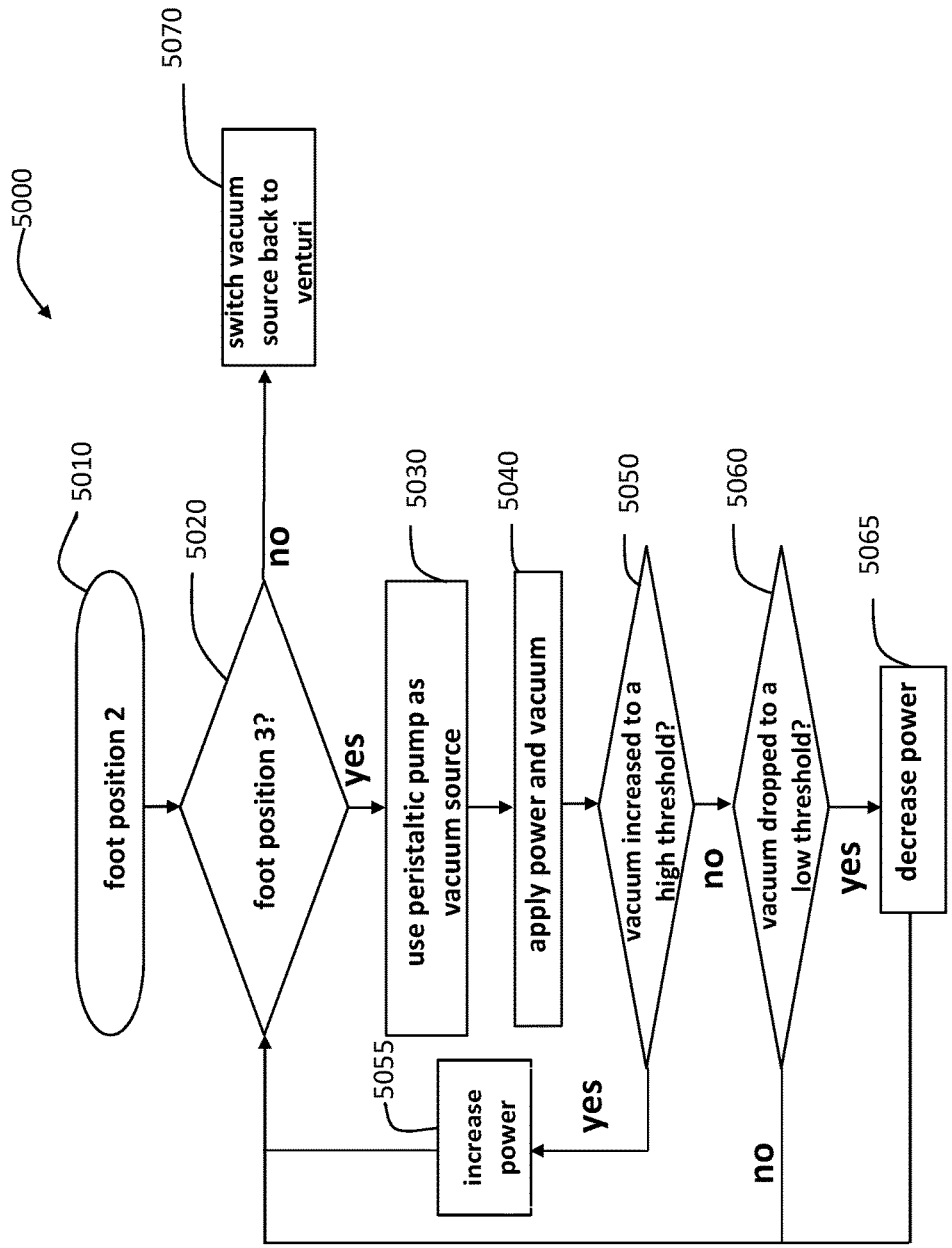

SYSTEMS AND METHODS FOR CONTROLLING VACUUM WITHIN PHACOEMULSIFICATION SYSTEMS

RELATED APPLICATIONS

This application claims priority to and is a divisional of U.S. application Ser. No. 13/236,386, filed Sep. 19, 2011, the entire contents of which are hereby incorporated in its entirety for all purposes as if fully set forth herein.

FIELD OF THE INVENTION

The field of the invention relates to systems and methods for cataract surgery, and more particularly to systems and methods for controlling vacuum within phacoemulsification systems.

BACKGROUND OF THE INVENTION

A number of medically recognized techniques are utilized for cataractous lens removal based on, for example, phacoemulsification, mechanical cutting or destruction, laser treatments, water jet treatments, and so on.

The phacoemulsification method includes emulsifying, or liquefying, the cataractous lens with ultrasonic power and then removing the emulsified material out of the eye. A phacoemulsification system 5 known in the art is shown in FIG. 1. The system 5 generally includes a phacoemulsification handpiece 10 coupled to an irrigation source 30 and an aspiration (or vacuum) pump 40. The handpiece 10 includes a needle 15 at the distal tip (shown within the anterior chamber of the patient's eye 1) that is ultrasonically vibrated to emulsify the cataractous lens within the patient's eye 1. The handpiece 10 further includes an irrigation port 25 proximal to the distal tip of the needle 15, which is coupled to an irrigation source 30 via an irrigation line 35, and an aspiration port 20 at the distal tip of the needle 15, which is coupled to an aspiration pump 40 via an aspiration line 45. Concomitantly with the emulsification, fluid from the irrigation source 30, which is typically an elevated bottle of saline solution, is irrigated into the eye 1 via the irrigation line 35 and the irrigation port 25, and the irrigation fluid and emulsified cataractous lens material are aspirated from the eye 1 by the aspiration pump 40 via the aspiration port 20 and the aspiration line 45. Other medical techniques for removing cataractous lenses also typically include irrigating the eye and aspirating lens parts and other liquids. Additionally, some procedures may include irrigating the eye 1 and aspirating the irrigating fluid without concomitant destruction, alteration or removal of the lens, e.g., with ultrasonic power.

Aspiration can be achieved with a variety of different aspiration pumps 40 known in the art. The two most common types are (1) volumetric flow or positive displacement pumps (also referred to as flow-based pumps such as peristaltic or scroll pumps) and (2) vacuum-based pumps (such as venturi, diaphragm, or rotary-vane pumps). Each type has its own general advantages and disadvantages. Turning to FIG. 2, an example peristaltic flow pump 50 is illustrated. In this configuration, the aspiration line 45 is in direct contact with a rotating pump head 50 having rollers 52 around its perimeter. As the pump head 50 rotates clockwise, the rollers 52 press against the line 45 causing fluid to flow within the line 45 in the direction of the rollers 52. This is referred to as a volumetric flow pump because the pump 50 directly controls the volume or rate of fluid flow. An advantage with this type of pump 50 is that the rate of fluid flow can be easily and precisely controlled by adjusting the rotational speed of the pump head 50.

Turning to FIG. 3, an example vacuum-based pump 60 is illustrated. This type of pump indirectly controls fluid flow by controlling the vacuum within the fluidic circuit. For example, the vacuum-based pump 60 can be a pneumatic pump (e.g., a venturi pump) that creates a pressure differential in a drainage cassette reservoir 65 that causes the fluid to be sucked from the aspiration line 45 into the drainage cassette reservoir 65. Thus, instead of pushing fluid through the aspiration line 45 like the flow pump 50, the fluid is essentially pulled by vacuum through the line 45. The rate of fluid flow generated by a vacuum-based pump is generally higher than the rate of fluid flow generated by a volumetric flow based pump because the vacuum-level is generally higher; however, the control of the rate of fluid flow generally involves a different control mechanism.

As is well known, for these various surgical techniques it is necessary to maintain a stable volume of liquid in the anterior chamber of the eye, and this is accomplished by irrigating fluid into the eye at the same rate as aspirating fluid and lens material. For example, see U.S. Pat. No. 5,700,240, to Barwick et. al, filed Jan. 24, 1995 ("Barwick") and U.S. Pat. No. 7,670,330 to Claus et. al, filed Mar. 21, 2005 ("Claus"), which are both hereby incorporated by reference in their entirety. During phacoemulsification, it is possible for the aspirating phacoemulsification handpiece 10 to become occluded. This occlusion is caused by particles blocking a lumen or tube in the needle 15 of the handpiece 10, e.g., the aspiration port 20 or irrigation port 25. In the case of volumetric flow based pumps, this blockage can result in increased vacuum (i.e. increasingly negative pressure) in the aspiration line 45 and the longer the occlusion is in place, the greater the vacuum. In contrast, with a vacuum-based pump, this blockage can result in a volumetric fluid flow drop off near the aspiration port 20. In either case, once the occlusion is cleared, a resulting rush of fluid from the anterior chamber into the aspiration line 45 can outpace the volumetric flow of new fluid into the eye 1 from the irrigation source 30.

The resulting imbalance of incoming and outgoing fluid can create an undesirable phenomenon known as post-occlusion surge or fluidic surge, in which the structure of the anterior chamber moves rapidly as fluid is replaced due to the dynamic change in the rate of fluid flow and pressure. Such post-occlusion surge events may lead to eye trauma. The most common approach to preventing or minimizing the post-occlusion surge is to quickly adjust the vacuum-level or rate of fluid flow in the aspiration line 45 and/or the ultrasonic power of the handpiece 10 upon detection of an occlusion. Many surgeons rely on their own visual observations to detect the occlusion; however, because of the unpredictable and time-sensitive nature of the problem, a reliable computer-based detection and response system is preferable.

For current systems with volumetric flow pumps 50, if an occlusion occurs, the flow rate will decrease at the aspiration port 20 and the vacuum level within the aspiration line 45 between the pump 50 and the handpiece 10 will increase. Thus, a computer-based system (not shown) can utilize a vacuum sensor 55 placed on the aspiration line 45 to detect the vacuum increase and respond accordingly (an example of such a system is described in U.S. Pat. No. 5,700,240, to Barwick et. al, filed Jan. 24, 1995 and U.S. Pat. No. 7,670,330 to Claus et. al, filed Mar. 21, 2005). For current systems with vacuum-based pumps 60, however, the vacuum level within the aspiration line 45 is tied to the vacuum power generated by the pump 60 and thus, may not be an effective indicator of whether an occlusion has occurred. Accordingly, an improved system and method for controlling the rate of fluid flow in vacuum based systems on the detection of occlusion within a fluid circuit is desirable.

SUMMARY OF THE INVENTION

The field of the invention relates to systems and methods for cataract surgery, and more particularly to systems and methods for controlling vacuum within phacoemulsification systems. In one embodiment, a phacoemulsification system may include a phacoemulsification handpiece having a needle. The needle is coupled to a power source configured to cause the needle to be ultrasonically vibrated during operation and an aspiration source. The system further includes a footpedal that defines a first position and a second position. The system also includes a computer program product operatively coupled to the phacoemulsification handpiece and the footpedal, the computer program product having a computer-usable medium having a sequence of instructions which, when executed by a processor, causes said processor to execute a process that controls power from the power source and vacuum from the aspiration source applied to the phacoemulsification handpiece.

The process includes the steps of providing the vacuum at a first vacuum level to the handpiece when the footpedal is at the first position; providing power to the handpiece when the footpedal is at the second position; and reducing the vacuum to a second vacuum level when the footpedal transitions from the first position to the second position.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the inventions are obtained, a more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

FIG. 2 is a diagram of a phacoemulsification system having a flow-based aspiration pump known in the art.

FIG. 3 is a diagram of a phacoemulsification system having a vacuum-based aspiration pump known in the art.

FIG. 4 is a functional block diagram of a phacoemulsification system in accordance with a preferred embodiment of the present invention;

FIG. 8*b* is chart illustrating an exemplary vacuum modulation in accordance with a preferred embodiment of the present invention.

FIG. 11*b* is another flowchart of a process in accordance with a preferred embodiment of the present invention.

DETAILED DESCRIPTION OF THE PREFERRED EMBODIMENTS

Figure 1:
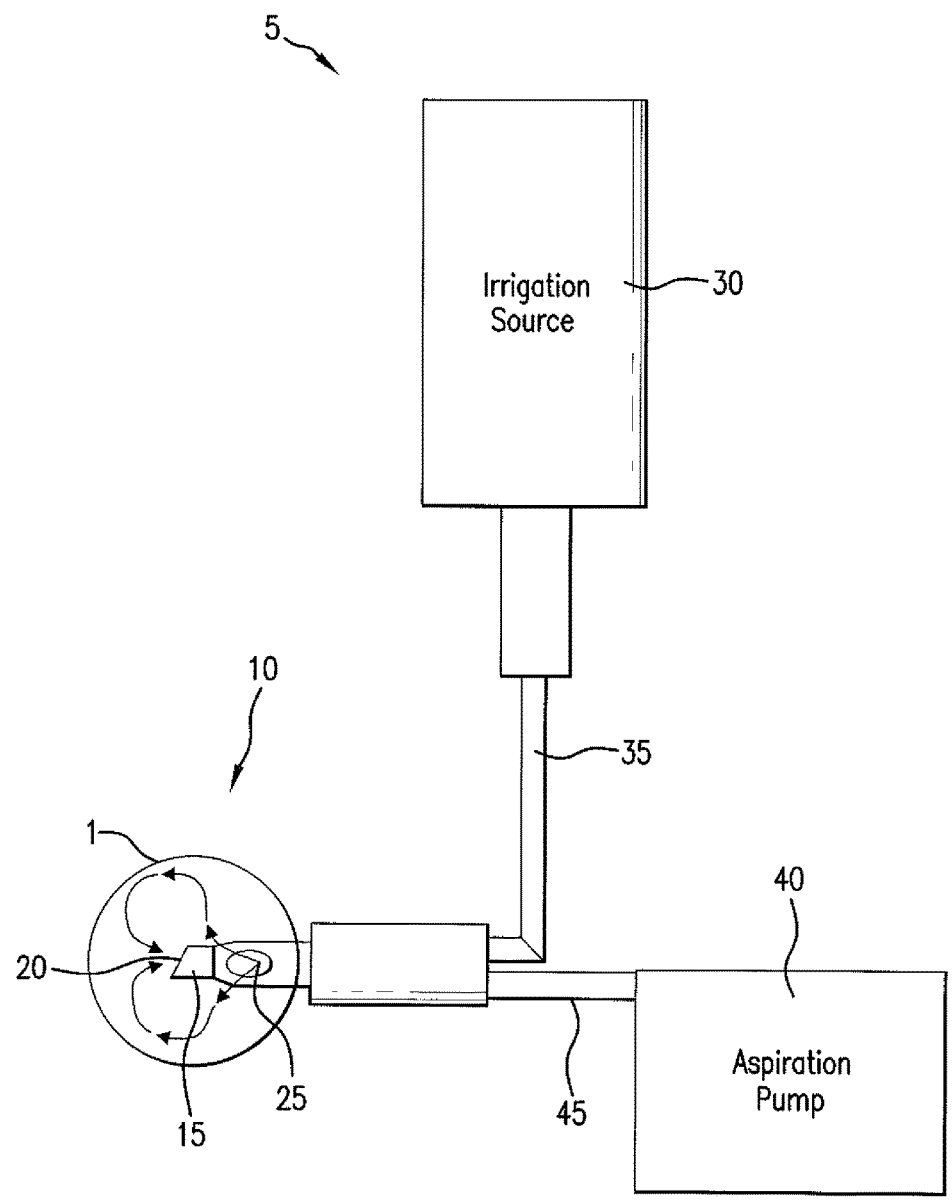
FIG. 1 is a diagram of a phacoemulsification system known in the art.

As described above, phacoemulsification typically involves the interplay of three key elements: power (ultrasonic power), vacuum (or aspiration), and irrigation fluid. Turning to FIG. 4, an exemplary system 100 that allows for control of these elements during phacoemulsification is further illustrated in block diagram form. The system 100 has a control unit 105, indicated by the dashed lines in FIG. 4 that includes a source of ultrasonic power 107 coupled to a handpiece 104 via line 102, a microprocessor computer 109 that provides control outputs to ultrasonic power level controller 111 that controls the ultrasonic power source 107. Ultrasonic power is delivered to eye 106 via handpiece 104 as illustrated by line 117.

The control unit 105 further includes an aspiration source 115—which may be a vacuum-based pump, such as a venturi-based-pump described above, a flow-based pump, such as a peristaltic-based pump described above, or a combination of a vacuum-based pump and a flow-based pump. Fluid aspirated from eye 106 via handpiece 104 is illustrated by line 108. The vacuum level of the aspiration source 115 applied to handpiece 104 via line 110 is controlled and monitored by computer 109. The system 100 further includes an irrigation fluid source 101 that is fluidly coupled to the handpiece 104. Irrigation fluid is delivered to eye 106 via handpiece 104 as illustrated by line 116. The rate of fluid provided to the handpiece 104 is also controlled by computer 109 of the control unit 105.

The block representation of the handpiece 104 includes a needle and electrical means (not shown), typically a piezoelectric crystal, for ultrasonically vibrating the needle. The handpiece/needle 104 is used to apply the elements above to a patient's eye, or affected area or region, indicated diagrammatically by block 106.

The control unit 105 may further include a user interface console, such as a touch screen monitor (not shown), to the computer 109 to allow the surgeon/operator to preset various system parameters. User defined system parameters may include, but are not limited to, selecting pulse shape amplitude mode, setting maximum allowable vacuum from aspiration source, minimum pulse shape amplitude, maximum pulse shape amplitude and irrigation rates.

Figure 5:
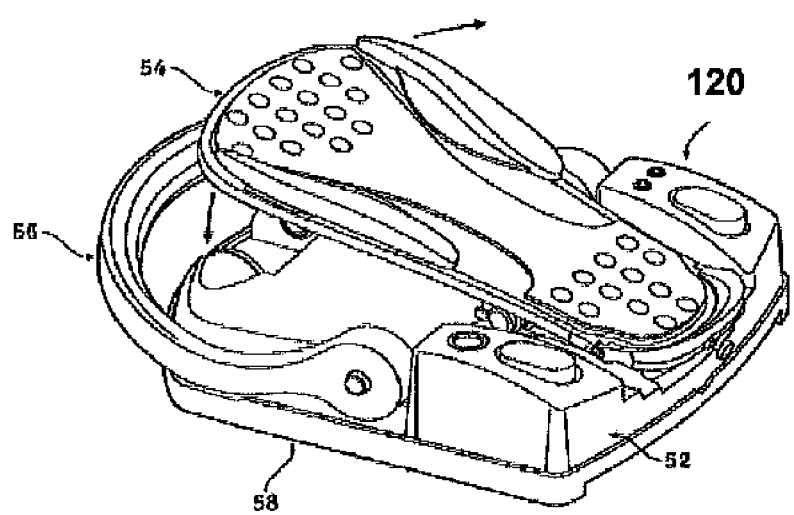
FIG. 5 is a perspective view of a footpedal suitable for use with the present invention.
Figure 6:
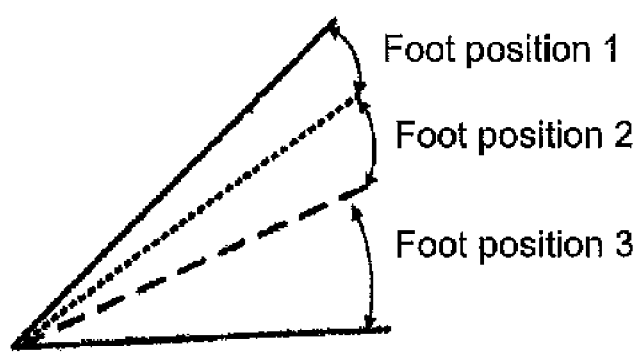
FIG. 6 is a diagram showing an exemplary configuration for the footpedal shown in FIG. 5.

A foot pedal 120 coupled to the computer 109 may be utilized to enable a surgeon/operator to control the irrigation source 101, the power source 107, and the aspiration source 115. Turning to FIG. 5, an exemplary foot pedal 120 is shown, which is described in U.S. patent application Ser. No. 12/613,562, U.S. Publication No. 2011/0098721 A1, filed Nov. 6, 2009, for "Adjustable Foot Pedal Control for Ophthalmic Surgery"—incorporated herewith in its entirety. The foot pedal 120 includes a platform or footswitch 54 mounted to a base 52. The base 52 has an undercarriage 58 arranged to lie flat on a ground surface and also a carrying handle 56. Footswitch 54 mounts on the base 52 to provide a movable control surface for the user. In one embodiment, footswitch 54 may be mounted for rotational yaw or horizontal movement relative to the base 52, as seen by the movement arrows in FIG. 5. Alternatively, the footswitch 54 may be mounted for pivoting movement in a vertical plane (pitch), as in a standard car accelerator-type pedal or as shown in FIG. 5, or may be a dual-control footswitch capable of both yaw and pivoting movement. As is known in the art, the computer 109 may include a computer-usable medium having a sequence of instructions which, when executed by a processor, causes said processor to execute a process that controls the elements above based on the displacement of the foot pedal 120. For example, FIG. 6 shows typical relative pitch displacement functions of the footswitch 54 communicatively coupled to computer 109 in which foot position 1 controls the irrigation, foot position 2 controls irrigation/aspiration and foot position 3 provides for control of ultrasound power delivery; and/or duty cycle. Further description of the operation of the foot pedal 120 can be found in U.S. patent application Ser. No. 11/560,333, U.S. Publication No. 2007/0073309 A1, filed Nov. 15, 2006, for "Control of Pulse Duty Cycle Based Upon Footswitch Displacement"—also incorporated herewith in its entirety.

As mentioned above, for phacoemulsification systems 100 using vacuum-based pumps such as venturi, diaphragm, or rotary-vane-based pumps as aspiration sources 115, the vacuum level within the aspiration line 110 is tied to the vacuum power generated by the source 115, and thus, may not be an effective indicator of whether an occlusion has occurred. As a result, surgeons tend to use lower vacuum levels to avoid post-occlusion, use a smaller gauge phaco tip to restrict the inflow of fluid, immediately release the footswitch 54 following the application of power to reduce the maximum allowable vacuum level, and/or use flow restrictors. Though each of these action items may be able to reduce the risk of post-occlusion surge, each one can undesirably lengthen the time of surgery and still allow for human error.

Figure 7:
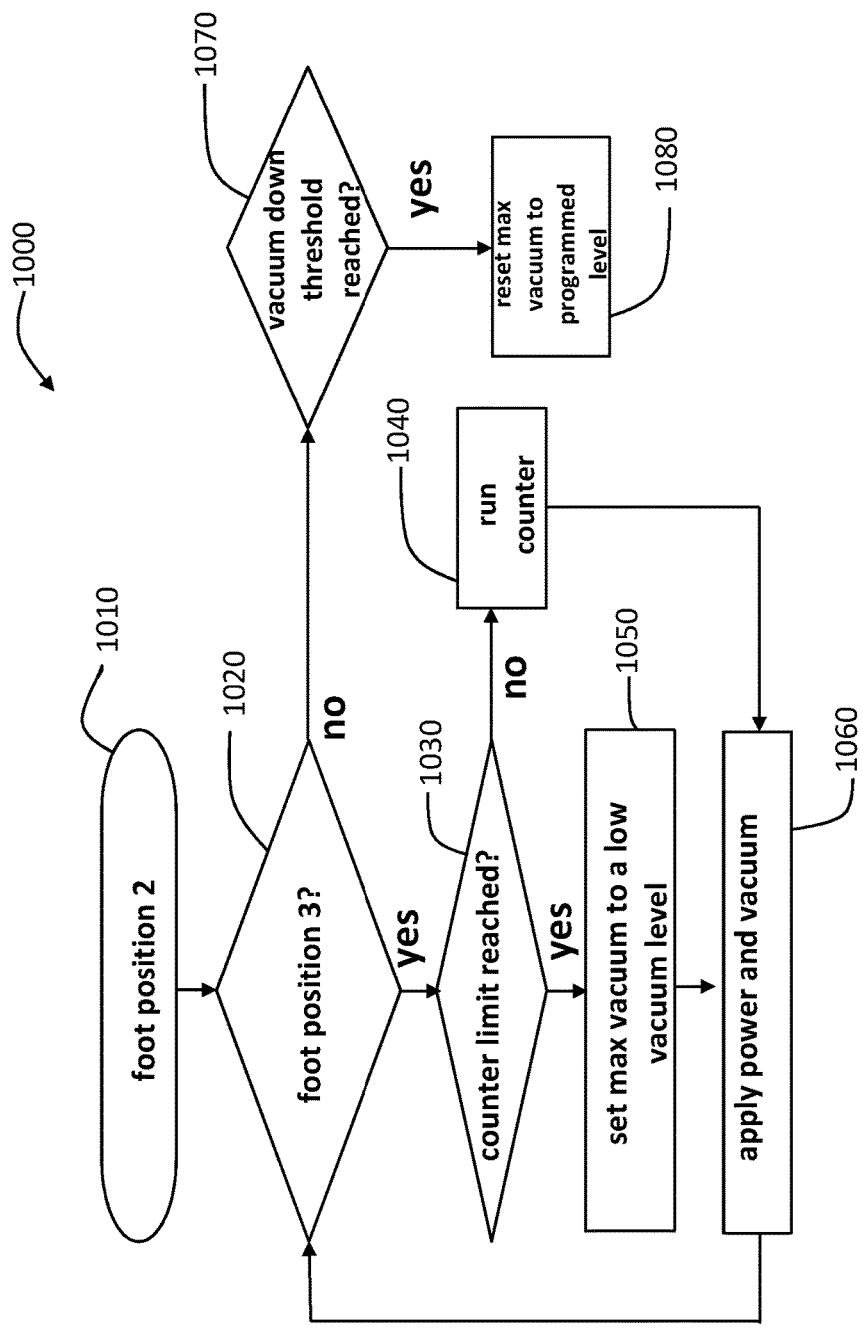
FIG. 7 is a flowchart of a process in accordance with a preferred embodiment of the present invention.

One approach to address this issue is shown in FIG. 7, which illustrates a process 1000 that may be executed within computer 109. Starting with the footswitch 54 displaced at foot position 2 (starting block 1010), if the user displaces or transitions the footswitch 54 to foot position 3 (decision block 1020), as described above, not only is vacuum applied to the handpiece 104, but ultrasound power is delivered as well (action block 1060). As one of ordinary skill in the art would appreciate, an experienced surgeon would depress the footswitch 54 from foot position 1 to foot position 2 to apply vacuum to grab hold of a particular piece of cataract particle at the tip of the needle 104 to emulsify and remove. Often, the control is set up such that the vacuum level linearly rises as the surgeon depresses the footswitch 54 from the foot position 1/2 transition to the foot position 2/3 transition until the maximum allowable vacuum level ("Max Vac") is reached (e.g., 300 mm Hg), and vice versa. For example, see U.S. Pat. No. 7,670,330 to Claus et. al, filed Mar. 21, 2005. Additionally, the control may be set up such that a transition from the foot position 1/2 to the foot position 2/3 linearly raises the vacuum level from a non-zero value (e.g., 100 mm Hg). When the tip of the needle of the handpiece 104 makes contact with the particle and is able to grab hold of it (with the help of the aspiration source 115), the surgeon would then further transition the footswitch 54 into foot position 3, to apply the ultrasonic power that would emulsify the particle for aspiration. Subsequently, an actual occlusion may occur or the existence of an occlusion at the handpiece needle 104 can be inferred if the surgeon stays in foot position 3 for a period of time.

As illustrated in FIG. 7, in light of the above, a feature can be added to the control in computer 109 that allows for a pre-determined or user-chosen "chamber stabilization" ("CS") setting to be enabled. If the CS setting is enabled, the process 1000 may proceed as follows. An actual occlusion may occur or the existence of an occlusion can be inferred if the footswitch 54 transitions into foot position 3 and stays in foot position 3 for a certain programmable period of time, e.g., in the hundreds of milliseconds range (decision block 1030 and action block 1040). In one embodiment, this programmable period of time is between 100 ms and 5000 ms. In response, the maximum allowable vacuum level, Max Vac, from the aspiration source 115 can immediately be adjusted and dropped to a lower, safer value, in the event that the occlusion clears before the surgeon expects it to (action block 1050) (e.g., from 300 mmHg to 200 mmHg). During this period of time, there has been no change in the surgeon's footswitch 54 position, nor has an assistant been required to modify any setting on the system. Accordingly, the process 1000 provides the advantage of reducing manual input and accordingly enables the physician to concentrate on the procedure. This lower vacuum level should be sufficient to maintain the hold of the particle to allow the surgeon to continue to apply power or use another instrument to manipulate the particle and clear the occlusion.

After the occlusion has cleared, the surgeon may release the footswitch 54 from foot position 3 (decision block 1020) to disable the application of ultrasonic power. To disable the CS feature, if the aspiration source 115 is linearly controlled as described above and if the surgeon releases the footswitch 54 to a point where the vacuum level drops below a certain threshold ("down threshold"), e.g., 100 mmHg, for example at a point near the middle or beginning of foot position 2 (decision block 1070) then Max Vac is reset to the programmed level, e.g., 300 mmHg in the example above (action block 1080). In the alternative, or additionally, the surgeon may simply reset Max Vac through another trigger, e.g., the yaw movement of footswitch 54 relative to base 52.

Figure 8A:
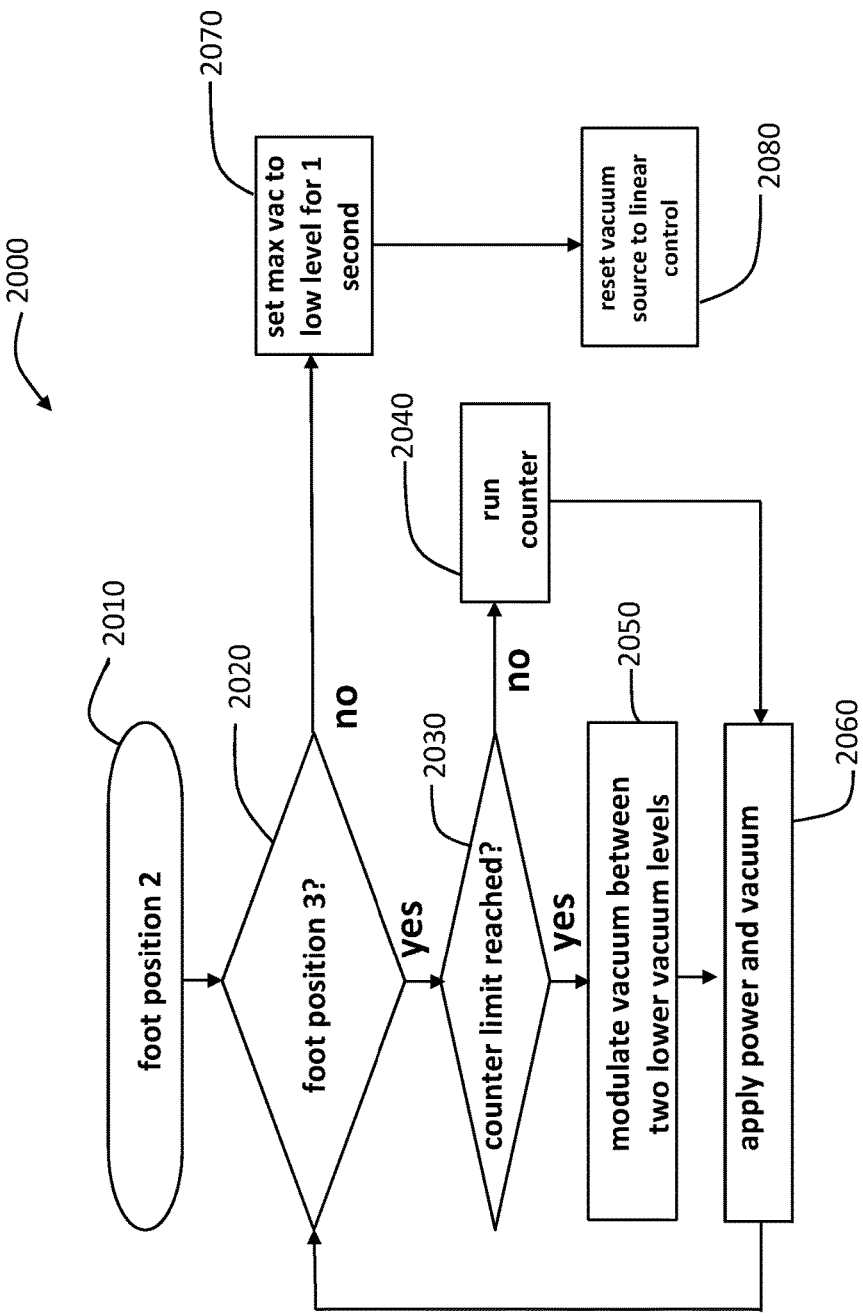
FIG. 8*a* is another flowchart of a process in accordance with a preferred embodiment of the present invention.

Turning to FIG. 8a, another process 2000 that provides for chamber stabilization in a vacuum-based phacoemulsification system 100 is shown Like with process 1000, process 2000 starts with the transition of the footswitch 54 from foot position 2 to foot position 3 (starting block 2010 and decision block 2020). As described above, this transition applies both vacuum and ultrasonic power to handpiece 104 (action block 2060). Also, an actual occlusion may occur or the existence of an occlusion can be inferred if the footswitch 54 transitions into foot position 3 and stays in foot position 3 for a certain programmable period of time, e.g., in the hundreds of milliseconds range (decision block 2030 and action block 2040). In one embodiment, this programmable period of time is between 100 ms and 5000 ms. In response, the vacuum source can reduce the Max Vac and modulate between two programmable lower vacuum levels, e.g., between 200 mm Hg and 100 mm Hg (action block 2050). This modulation will allow for the grasping of the particle at the higher level (e.g., 200 mm Hg) and reduce the risk of surge at the lower level (e.g., 100 mm Hg), and the modulation will further create a "shear" force to help break up the occlusion. Additionally, the application of power (in foot position 3) will create movement of the particle to allow inflow of irrigation fluid into the aspiration line 110, contributing to a balanced and stable anterior chamber of the eye 106.

In addition to programming the lower vacuum levels, the cycles between the modulation also can be programmed, as illustrated in FIG. 8*b*. For instance, the time that a particular vacuum level is maintained, t1 and t2, can each be programmed. For example, the time t2 at the higher vacuum level v2 (e.g., 200 mm Hg) can be maintained for 2 seconds whereas the time t1 at the lower vacuum level v1 (e.g., 100 mm Hg) can be maintained for 2 seconds. In yet another example, the time t2 at the higher vacuum level v2 (e.g., 200 mm Hg) can be maintained for 5 seconds whereas the time t1 at the lower vacuum level v1 (e.g., 100 mm Hg) can be maintained for 2 seconds. As noted above, in a vacuum-based system, the modulation of vacuum levels at times t1 and t2 can enable the system to control particle movements for enhanced destruction (i.e., emulsification) of an occlusion. What is shown in FIG. 8*b* is an exemplary square wave pattern; however, as one of ordinary skill in the art can appreciate, the process 2000 may be configured to provide modulation in a sine, triangle, or sawtooth wave pattern and/or a combination thereof.

Turning back to FIG. 8*a*, after the occlusion has cleared, the surgeon may release the footswitch 54 from foot position 3 (decision block 2020) to disable the application of ultrasonic power. To disable the chamber stability feature described above, when the footswitch 54 travels back to foot position 2, the Max Vac is set to 100 mm Hg for a certain period, e.g., 1 second (action block 2070), and the linear control of the aspiration source 115 is returned with the vacuum level dependent on location of the footswitch in foot position 2 (action block 2080).

Figure 9:
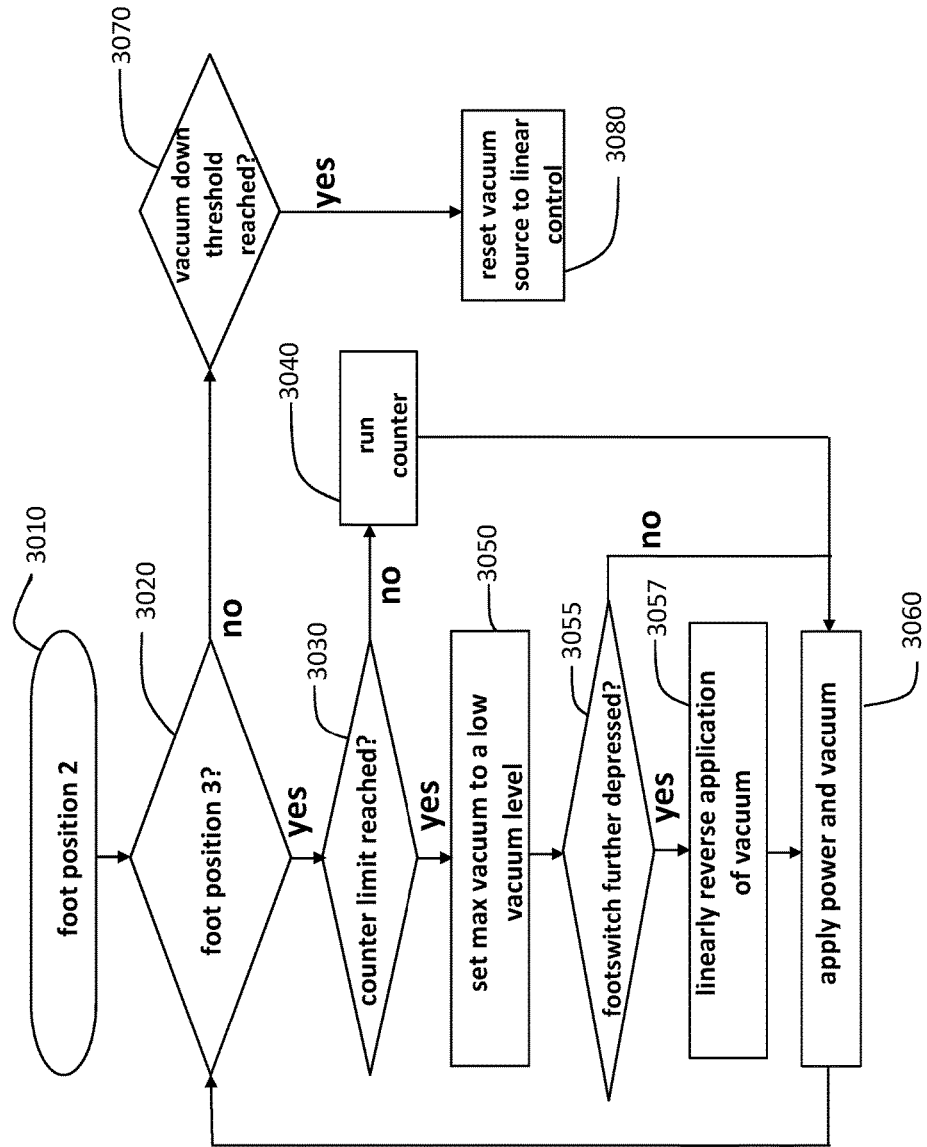
FIG. 9 is another flowchart of a process in accordance with a preferred embodiment of the present invention.

Turning to FIG. 9, another process 3000 that provides for chamber stabilization in a vacuum-based phacoemulsification system 100 is shown Like with process 1000, process 3000 starts with the transition of the footswitch 54 from foot position 2 to foot position 3 (starting block 3010 and decision block 3020). As described above, this transition applies both vacuum and ultrasonic power to handpiece 104 (action block 3060). Also, an actual occlusion may occur or the existence of an occlusion can be inferred if the footswitch 54 transitions into foot position 3 and stays in foot position 3 for a certain programmable period of time, e.g., in the hundreds of milliseconds range (decision block 3030 and action block 3040). In response, the computer 109 and aspiration source 115 can reduce the Max Vac to a lower level, e.g., 200 mm Hg (action block 3050). Further, if the footswitch 54 is further depressed (decision block 3055), the vacuum level is further reduced concomitantly with the depression of the footswitch 54 until it reaches a base vacuum level, e.g., 100 mm Hg (action block 3057).

After the occlusion has cleared, the surgeon may release the footswitch 54 from foot position 3 (decision block 3020) to disable the application of ultrasonic power. To disable the chamber stability feature described above, the surgeon can release the footswitch 54 to a point where the vacuum level drops below a certain threshold ("down threshold"), e.g., 100 mmHg, for example at a point near the middle or beginning of foot position 2 (decision block 3070) then Max Vac is reset to the programmed level, e.g., 300 mmHg in the example above and linear control of the aspiration source 115 is returned (action block 3080). In the alternative, or additionally, the surgeon may simply disable the CS feature through another trigger, e.g., a switch on the handpiece 104 (not shown) or the yaw movement of footswitch 54 relative to base 52. Moreover, the release described in process 2000 may be utilized, i.e., when the footswitch 54 travels back to foot position 2, the Max Vac is set to 100 mm Hg for a certain period, e.g., 1 second, and linear control of the aspiration source 115 is enabled with the vacuum level dependent on location of the footswitch in foot position 2.

Figure 10:
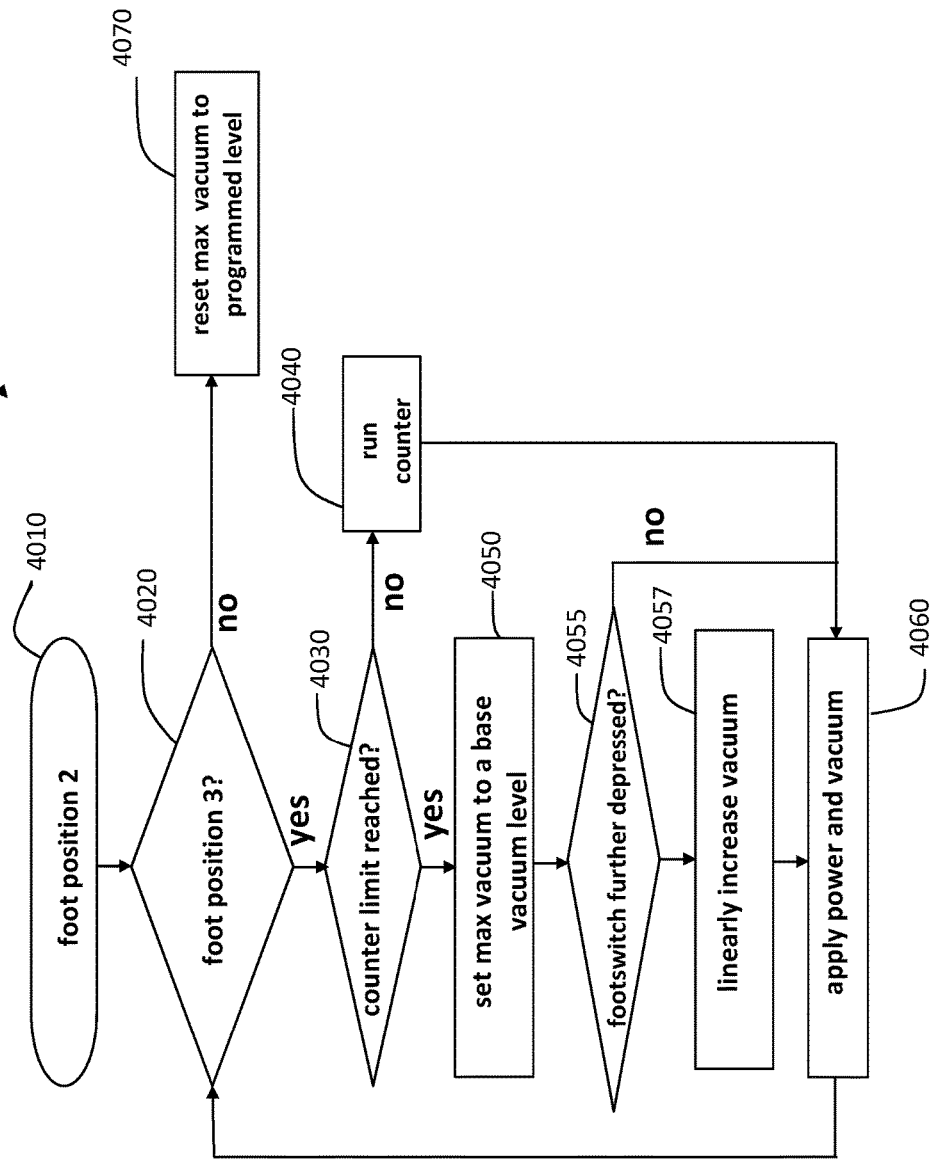
FIG. 10 is another flowchart of a process in accordance with a preferred embodiment of the present invention.

Turning to FIG. 10, another process 4000 that provides for chamber stabilization in a vacuum-based phacoemulsification system 100 is shown Like with process 1000, process 4000 starts with the transition of the footswitch 54 from foot position 2 to foot position 3 (starting block 4010 and decision block 4020). As described above, this transition applies both vacuum and ultrasonic power to handpiece 104 (action block 4060). Also, an actual occlusion may occur or the existence of an occlusion can be inferred if the footswitch 54 transitions into foot position 3 and stays in foot position 3 for a certain programmable period of time, e.g., in the hundreds of milliseconds range (decision block 4030 and action block 4040). In response, the vacuum source can reduce the Max Vac to a base level, e.g., 100 mm Hg (action block 4050). Further, if the footswitch 54 is further depressed (decision block 4055), the vacuum level increases concomitantly with the depression of the footswitch 54 until it reaches an adjusted max vac level, e.g., 200 mm Hg (action block 4057).

After the occlusion has cleared, the surgeon may release the footswitch 54 from foot position 3 (decision block 2020) to disable the application of ultrasonic power. The CS feature may also be released as well (action block 4070). In the alternative, or additionally, the surgeon may simply disable the CS feature through another trigger, e.g., a switch on the handpiece 104 (not shown) or the yaw movement of footswitch 54 relative to base 52.

Figure 11A:
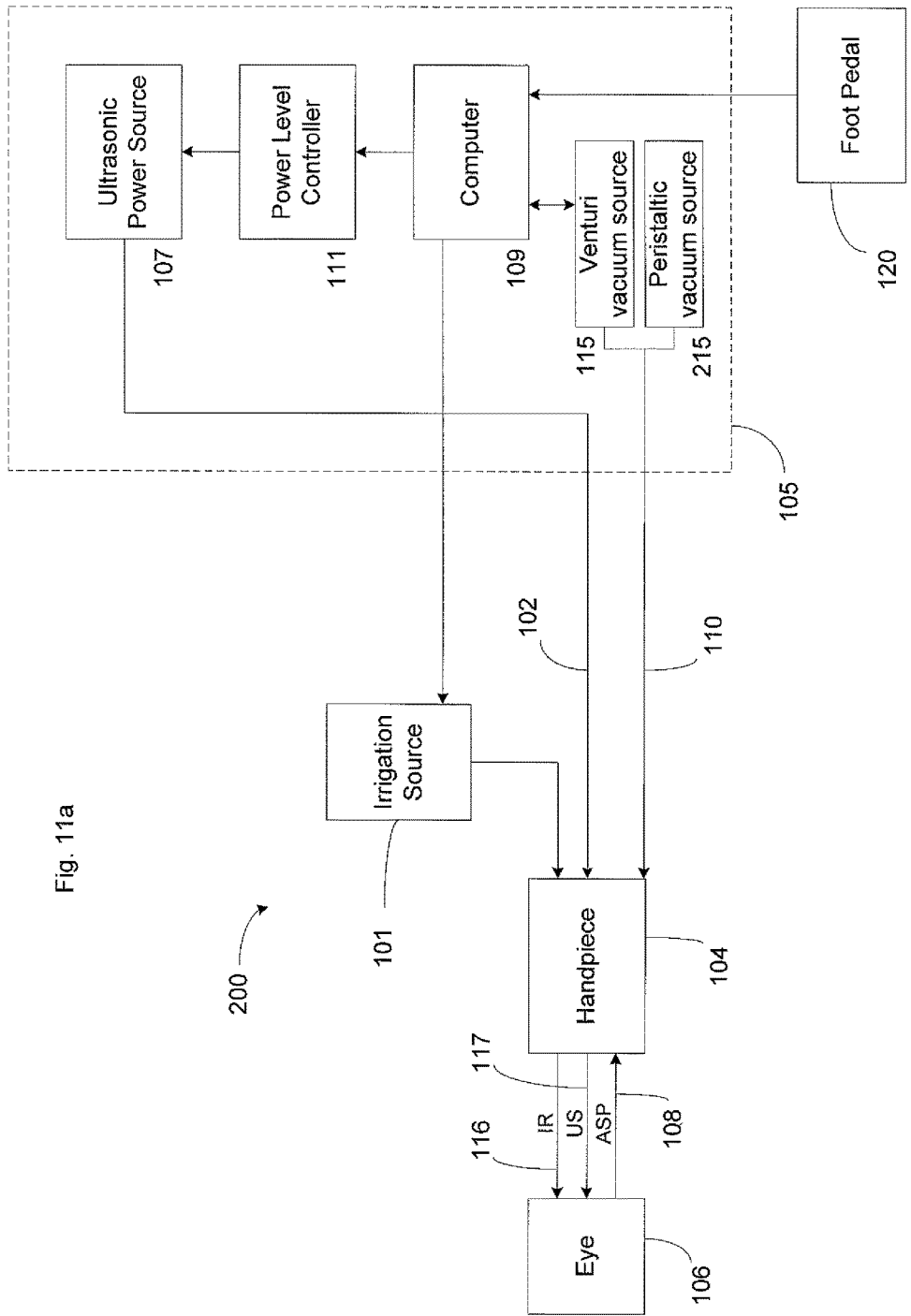
FIG. 11*a* is a diagram of a phacoemulsification system having a venturi-based pump and a peristaltic-based pump known in the art.

Turning to FIG. 11*b*, another process 5000 that provides for chamber stabilization in a vacuum-based phacoemulsification system 100 is shown. This process is based on a dual pump system 200, as shown in FIG. 11*a*. In a dual pump system 200, two types of aspiration sources are included, a vacuum based source, such as a venturi-based aspiration source 115, and a flow-based source, such as a peristaltic-based source 215. The computer 109 can serve as a switch to determine which aspiration source 115/215 is applied to aspiration line 110 and the handpiece 104. The foot pedal 120 may also be used to trigger the switch between one aspiration source and the other 115/215, e.g., the yaw movement of footswitch 54 to the left of base 52 to operate pump 115 and the yaw movement of footswitch 54 to the right of the base 52 to operate second pump 215. In one embodiment, the ramp-up/start-up of the newly employed aspiration source will typically start before the ramp-down of the previously used source has completed. Thus there is no time delay between switching of the sources and/or significant change (increase or decrease) in vacuum or flow rate during the switching. Accordingly, switching between these two different types of aspiration flow may occur "on-the-fly" without halting of a corresponding irrigation flow, and without awaiting input from the system operator regarding that particular flow change. Further detail about an exemplary dual pump system 200 and the switch mechanism is described in U.S. patent application Ser. No. 12/614,093, U.S. Publication No. 2010/0280435 A1, filed Nov. 6, 2009 for "Automatically Switching Different Aspiration Levels and/or Pumps to an Ocular Probe," which is hereby incorporated by reference.

Turning back to FIG. 11b, like with process 1000, process 5000 starts with the transition of the footswitch 54 from foot position 2 to foot position 3 (starting block 5010 and decision block 5020). If the footswitch 54 transitions into foot position 3 (decision block 5020), then the aspiration source can be switched from a vacuum-based aspiration source 115 to a flow-based pump 215 (action block 5030). This allows a vacuum sensor (not shown) coupled to aspiration line 110 to provide a reading indicating whether an occlusion exists or not based on measured vacuum level in the aspiration port of the handpiece/needle 104. In response, the system 200 may control at least one of: the supply of irrigation fluid, vacuum level, aspiration rate, and power applied to the handpiece 104. Specifically, the vacuum level may be controlled by lowering a maximum level of vacuum allowed during an occluded state of a surgical procedure. Such a system is described in U.S. Pat. No. 7,670,330 to Claus et. al, filed Mar. 21, 2005 and U.S. Pat. No. 7,785,336 to Staggs, filed Aug. 1, 2006, which are incorporated by reference in their entirety.

The peristaltic pump 215 can be preset to a maximum vacuum or a ratio of the maximum venturi-based source 115. As ultrasonic power is being applied (action block 5040), particle movement will cause vacuum level to fluctuate. If the vacuum level increases to a high threshold (decision block 5050), e.g., 300 mm Hg, the handpiece/needle 104 may be occluded with a particle. In that situation, large particles tend to be more readily emulsified when the particle is moved away from the handpiece/needle 104 tip. Therefore, it may then be desirable to determine whether additional energy is required to bump or move a large particle away from the tip of needle 104. As described in U.S. Pat. No. 7,670,330 to Claus et. al, filed Mar. 21, 2005 and U.S. Pat. No. 7,785,336 to Staggs, filed Aug. 1, 2006, increasing ultrasonic power proportional to an increase in a sensed aspiration vacuum pressure (e.g., increasing duty cycle or amplitude of the pulsed ultrasonic energy) allows for more effective emulsification of large and small particles (action block 5055). If, on the other hand, the particle is released or completely emulsified, the vacuum level will quickly drop, thus signifying completion of the emulsification process (decision block 5060). At this point, less or no ultrasonic power is needed to enable the particle to be drawn to the needle tip (action block 5065). If the user maintains the foot switch 54 in foot position 3 (decision block 5020), the peristaltic source 215 is still utilized (action block 5030) and thus, if an occlusion occurs again, the vacuum sensor may detect it (decision block 5050) and automatically increase power again (action block 5065). This process allows for less foot pedal 54 activity by the user with faster reaction time. The user can also transition back to foot position 2 (decision block 5020), thereby causing the system 200 to switch its aspiration source back to the venturi source 115 (action block 5070). Furthermore, the CS feature may also be released as well, e.g., through another trigger, e.g., the yaw movement of footswitch 54 relative to base 52.

As discussed above, upon a transition back to the venturi source 115 (action block 5070), the vacuum level of peristaltic source 215 may be controlled while the venturi source 115 is ramping/starting-up to affect an "on-the-fly" transition. Accordingly, as one of ordinary skill in the art would appreciate, system 200 controls the vacuum level of both aspiration sources 115/215 to maintain a stable vacuum level and to alleviate any spike in vacuum level occurring during the transition. In one embodiment, a transition from the peristaltic source 215 to the venturi source 115 may cause dips in the patient's eye if there is a mismatch in flow rate between the two sources 115/215. To avoid the mismatch in flow rate and to maintain a stable chamber, system 200 can adjust the vacuum level of the venturi source 115 to the actual vacuum measured while using the peristaltic source 215 prior to the transition. Following the transition, the venturi source 115 is allowed to ramp up to a setting that has been configured in the system 200 and the system 200 resumes normal operation.

In the event the system 200 transitions back from venturi source 115 to peristaltic source 215, the system 200 also provides a stable vacuum level during operation. This similarly requires maintaining constant flow rate between the two aspiration sources 115/215. However, as discussed above, while using venturi source 115, the vacuum level may not give an accurate indication of flow rate of the aspiration fluid. Nevertheless, it is possible to measure the flow rate of the fluid without contamination by measuring the air flow rate from the vacuum port using, e.g., an air flow sensor placed on the aspiration port 110. Accordingly, in one embodiment, as the air flow is proportional to the flow rate of the fluid, the flow rate of the aspiration fluid can be measured using air flow and the flow rate of the peristaltic source 215 can be similarly made to match the actual calculated vacuum while using the venturi source 115 prior to the transition. Following the transition, the peristaltic source 215 is allowed to ramp up to a setting that has been configured in the system 200 and the system 200 resumes normal operation.

Figure 12:
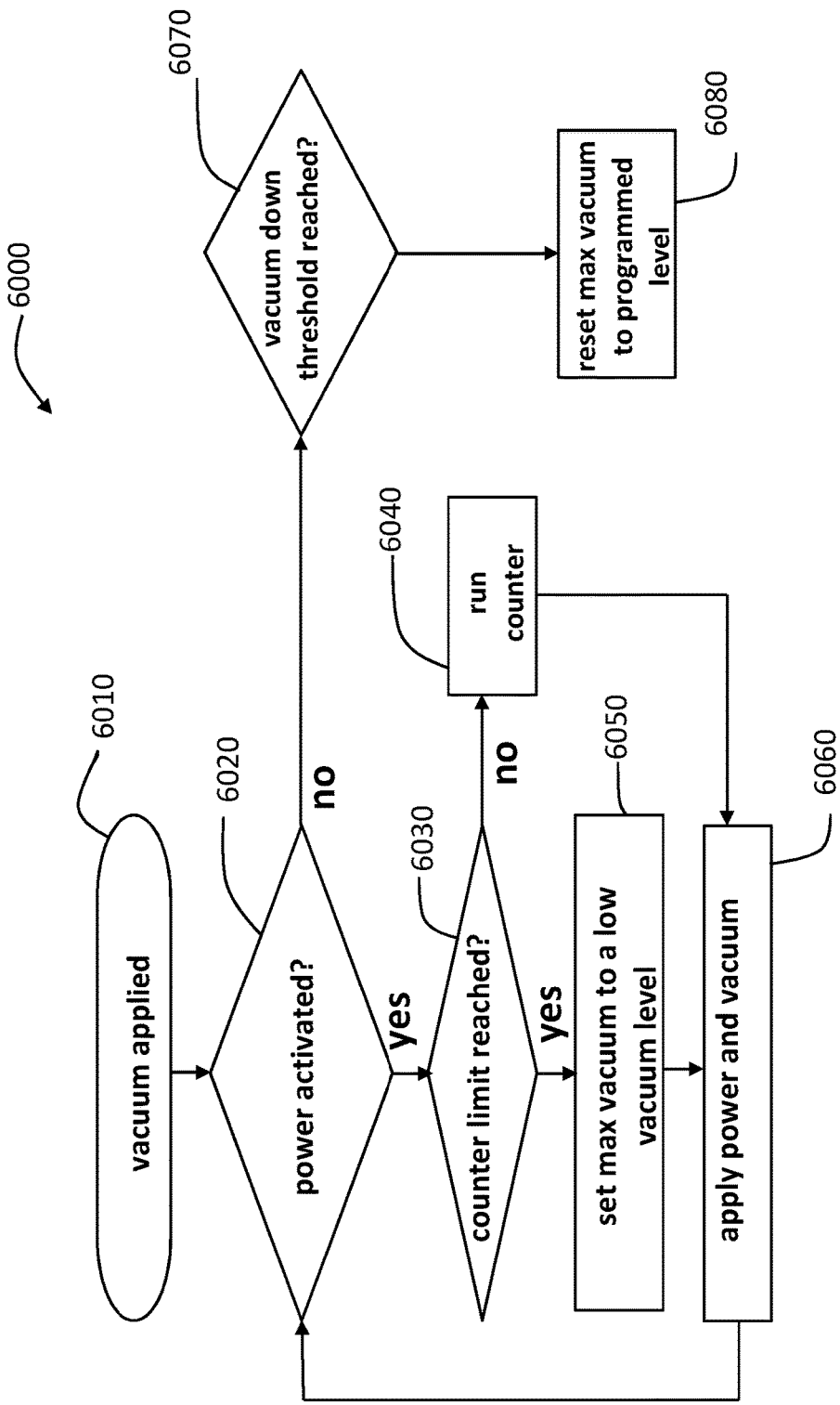
FIG. 12 is another flowchart of a process in accordance with a preferred embodiment of the present invention.

Turning to FIG. 12, a more general process 6000 that provides for chamber stabilization in a vacuum-based phacoemulsification system 100 is shown. The previous embodiments are based on the foot pedal 120 having a configuration as shown in FIGS. 5 and 6. However, other configurations may be utilized. For example, a hand controlled switch (not shown) may also be utilized. In yet another example, a voice command controller (not shown) may also be utilized. Turning back to FIG. 12, like with process 1000, process 6000 starts with the application of vacuum (action block 6010). If the user initiates the application of power (decision block 6020), and applies power for a certain programmable period of time, e.g., in the hundreds of milliseconds range (decision block 6030 and action block 6040), the existence of an occlusion can be inferred or an actual occlusion occurs. In response, the maximum allowable vacuum level, Max Vac, from the aspiration source 115 can immediately be adjusted and dropped to a lower, safer value, in the event that the occlusion clears before the surgeon expects it to (action block 6050) (e.g., from 300 mmHg to 200 mmHg).

After the occlusion has cleared, the surgeon may elect to disable power (decision block 6020). To disable the CS feature, if the aspiration source 115 is linearly controlled as described above and if the surgeon releases the vacuum controlled switch to a point where the vacuum level drops below a certain threshold ("down threshold"), e.g., 100 mmHg (decision block 6070), then Max Vac is reset to the programmed level, e.g., 300 mmHg in the examples above (action block 6080). In the alternative, or additionally, the surgeon may simply reset Max Vac through another trigger, e.g., the yaw movement of footswitch 54 relative to base 52 in the case where a foot pedal 120 is used.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention may appropriately be performed using different or additional process actions, or a different combination or ordering of process actions. For example, this invention is particularly suited for vacuum-based phacoemulsification systems, such as venturi-based systems; however, the invention can be used for any phacoemulsification system. Additionally and obviously, features may be added or subtracted as desired. Accordingly, the invention is not to be restricted except in light of the attached claims and their equivalents.

What is claimed is:

1. A method of controlling power from a power source and a vacuum from an aspiration source applied to a phacoemulsification handpiece, the handpiece having a needle coupled to the power source configured to cause the needle to be ultrasonically vibrated during operation, the needle further defining an aspiration port that is coupled to the aspiration source, a footpedal defining a first position and a second position, the method comprising:
   providing the vacuum at a first vacuum level to the handpiece up to a first maximum vacuum level when the footpedal is at the first position;
   providing power to the handpiece when the footpedal is at the second position;
   determining when the footpedal remains at the second position for a programmable period of time; and
   reducing the vacuum to a second vacuum level up to a new maximum vacuum level when the footpedal remains at the second position for the programmable period of time, the new maximum vacuum level is less than the first maximum vacuum level.

2. The method of claim 1, wherein the new maximum vacuum level is based on a predetermined setting that includes the transition of the footpedal from the first position to the second position displacing the footpedal at the second position for a programmable period of time.

3. The method of claim 1, further comprising modulating the vacuum between the second vacuum level and a third vacuum level, the third vacuum level is less than the new maximum vacuum level.

4. The method of claim 1, wherein the footpedal further defines a third position, and further comprising reducing the vacuum level to a third vacuum level when the footpedal transitions to said third position.

5. The method of claim 1, wherein the footpedal further defines a third position, and further comprising raising the new maximum vacuum level to an adjusted maximum vacuum level and raising the vacuum level up to the adjusted maximum level when the footpedal transitions to said third position, the adjusted maximum level is less than the first maximum vacuum level and greater than the new maximum vacuum level.

6. The method of claim 1, further comprising resetting the new maximum vacuum level to the first maximum vacuum level when the footpedal transitions back from the second position to the first position.

7. The method of claim 1, wherein the footpedal further defines a yaw position and further comprising resetting the new maximum vacuum level to the first maximum vacuum level when the footpedal transitions to said yaw position.

8. The method of claim 1, wherein the aspiration source is a vacuum-based pump or a combination of a vacuum-based pump and a flow-based pump.

9. The method of claim 1, wherein the aspiration source is a combination of a vacuum-based pump and a flow-based pump, the footpedal further defines a third position, and further comprising transitioning between the vacuum-based pump and flow-based pump when the footpedal transitions to said third position, the transition maintaining a stable vacuum level.

* * * * *